United States Patent
Liu et al.

(10) Patent No.: US 11,179,050 B2
(45) Date of Patent: Nov. 23, 2021

(54) METHOD FOR DETERMINING CUFF BLOOD PRESSURE

(71) Applicants: BOARD OF TRUSTEES OF MICHIGAN STATE UNIVERSITY, East Lansing, MI (US); UNIVERSITY OF MARYLAND, College Park, MD (US)

(72) Inventors: Jiankun Liu, East Lansing, MI (US); Mohsen Moslehpour, Sunnyvale, CA (US); Jin-Oh Hahn, Rockville, MD (US); Ramakrishna Mukkamala, Okemos, MI (US)

(73) Assignees: Board of Trustees of Michigan State University, East Lansing, MI (US); University of Maryland, College Park, College Park, MD (US)

( * ) Notice: Subject to any disclaimer, the term of this patent is extended or adjusted under 35 U.S.C. 154(b) by 681 days.

(21) Appl. No.: 15/758,401

(22) PCT Filed: Sep. 9, 2016

(86) PCT No.: PCT/US2016/051069
§ 371 (c)(1),
(2) Date: Mar. 8, 2018

(87) PCT Pub. No.: WO2017/044823
PCT Pub. Date: Mar. 16, 2017

(65) Prior Publication Data
US 2018/0256045 A1    Sep. 13, 2018

Related U.S. Application Data

(60) Provisional application No. 62/217,331, filed on Sep. 11, 2015.

(51) Int. Cl.
*A61B 5/022*    (2006.01)
*A61B 5/02*     (2006.01)
(Continued)

(52) U.S. Cl.
CPC ............ *A61B 5/02225* (2013.01); *A61B 5/02* (2013.01); *A61B 5/021* (2013.01); *A61B 5/022* (2013.01);
(Continued)

(58) Field of Classification Search
None
See application file for complete search history.

(56) References Cited

U.S. PATENT DOCUMENTS 5,423,322 A    6/1995    Clark et al.
5,590,662 A    1/1997    Hersh et al.
(Continued)

OTHER PUBLICATIONS

S. Yoon et al., "Simulation Of Estimating The Blood Pressure Using An Arterial Pressure-Volume Model", 2007 International Conference on Convergence Information Technology (ICCIT 2007), pp. 2181-2186 (2007).
(Continued)

*Primary Examiner* — Jacqueline Cheng
*Assistant Examiner* — Jairo H Portillo
(74) *Attorney, Agent, or Firm* — Harness, Dickey & Pierce, PLC

(57) ABSTRACT

Most automatic cuff blood pressure (BP) measurement devices are based on oscillometry. These devices estimate BP from the envelopes of the cuff pressure oscillations using fixed ratios. The values of the fixed ratios represent population averages, so the devices may be accurate only in subjects with normal BP levels. A patient-specific oscillometric BP measurement method was developed. The idea was to represent the cuff pressure oscillation envelopes with
(Continued)

a physiologic model and then estimate the patient-specific parameters of the model, which includes BP levels, by optimally fitting it to the envelopes.

13 Claims, 10 Drawing Sheets

(51) Int. Cl.
    *A61B 5/021*     (2006.01)
    *G16H 50/50*     (2018.01)
    *G06F 111/10*     (2020.01)

(52) U.S. Cl.
    CPC ...... *G16H 50/50* (2018.01); *A61B 2562/0247* (2013.01); *G06F 2111/10* (2020.01)

(56) References Cited

U.S. PATENT DOCUMENTS

| | | |
|---|---|---|
| 6,458,085 B1 | 10/2002 | Wu et al. |
| 6,733,461 B2 | 5/2004 | Bratteli |
| 6,767,328 B2 | 7/2004 | Kulik |
| 6,808,496 B2 | 10/2004 | Oka et al. |
| 6,893,403 B2 | 5/2005 | Kolluri et al. |
| 7,186,218 B2 | 3/2007 | Hersh et al. |
| 7,288,070 B2 | 10/2007 | Kolluri et al. |
| 7,775,987 B2 | 8/2010 | Hersh et al. |
| 2007/0167844 A1* | 7/2007 | Asada ................. A61B 5/6826 600/485 |
| 2010/0324384 A1 | 12/2010 | Moon et al. |
| 2010/0324429 A1 | 12/2010 | Leschinsky |
| 2012/0136605 A1 | 5/2012 | Addison et al. |
| 2014/0066788 A1 | 3/2014 | Mukkamala et al. |
| 2014/0066793 A1 | 3/2014 | Mukkamala et al. |
| 2014/0163402 A1 | 6/2014 | Lamego et al. |

OTHER PUBLICATIONS

T. Kim, et al., "A New Blood Pressure Measurement Using Dual-Cuffs", 2008 Computers in Cardiology, pp. 165-168 (2008).
J. Jilek, et al., "Dual-Cuff System Improves Noninvasive Blood Pressure Determination", Applied Electronics (AE), 2010 International Conference, pp. 2-5 (2010).
M. Forouzanfar, et al., "Mathematical Modeling and Parameter Estimation Of Blood Pressure Oscillometric Waveform", 2012 IEEE International Symposium on Medical Measurements and Applications Proceedings, pp. 1-6 (2012).
C. Babbs, "Oscillometric Measurement Of Systolic And Diastolic Blood Pressures Validated In A Physiologic Mathematical Model", Biomedical Engineering Online, vol. 11, p. 45 (2012).
M. James "Simplified Model For The Design Of An Oscillometric Blood Pressure Measuring System", A thesis presented to The University of Guelph, Guelph, Ontario, CA (2012).

* cited by examiner

METHOD FOR DETERMINING CUFF BLOOD PRESSURE

CROSS-REFERENCE TO RELATED APPLICATIONS

This application is a 371 National Phase of PCT/US2016/051069, filed on Sep. 9, 2016, and published in English as WO 2017/044823 A1 on Mar. 16, 2017, which claims the benefit of U.S. Provisional Application No. 62/217,331 filed on Sep. 11, 2015. The entire disclosures of the above applications are incorporated herein by reference.

GOVERNMENT SUPPORT CLAUSE

This invention was made with government support under EB-018818 awarded by the National Institutes of Health and under IIS-1404436 and IIS-1403004 awarded by the National Science Foundation. The government has certain rights in the invention.

FIELD

The present disclosure relates to a patient-specific oscillometric blood pressure measurement.

BACKGROUND

Oscillometry is a widely used approach for automatic cuff blood pressure (BP) measurement. In this approach, a cuff placed on typically the upper arm is inflated and then deflated while the pressure inside the cuff is measured. As shown in FIG. 1, the resulting cuff pressure not only rises and falls but also shows small oscillations indicating the pulsatile blood volume within the brachial artery underneath the cuff. The amplitude of these oscillations changes with the applied cuff pressure, as the brachial artery compliance varies with transmural pressure (i.e., BP—cuff pressure). Blood pressure is then estimated from the oscillation amplitudes and cuff pressure.

Blood pressure estimation is conventionally performed via fixed ratios. As shown in FIG. 1, first, mean BP (MP) is estimated as the cuff pressure at which the oscillation amplitude is maximal, since the brachial artery compliance peaks near zero transmural pressure. Then, systolic and diastolic BP (SP and DP) are each estimated as the cuff pressure at which the oscillation amplitude is some fixed ratio of the maximal value. While current devices do not disclose their exact methods for estimating BP, they are believed to employ the fixed-ratio method or some variant thereof. Since such methods are based on population averages, the devices work well only in subjects with normal BP levels. Indeed, the accuracy of the devices is known to be compromised in subjects with large artery stiffening and thus high pulse pressure (PP=SP−DP)–a common condition that occurs with aging and disease.

In this disclosure, a patient-specific method is presented for estimating blood pressure from an oscillometric cuff pressure waveform.

This section provides background information related to the present disclosure which is not necessarily prior art.

SUMMARY

This section provides a general summary of the disclosure, and is not a comprehensive disclosure of its full scope or all of its features.

A method is presented for determining mean blood pressure for a subject. The method includes: measuring cuff pressure using an automatic cuff device during a blood pressure measure of the subject; deriving an oscillogram from the measured cuff pressure, where the oscillogram is an amplitude of oscillations in the measured cuff pressure as a function of the measured cuff pressure; representing the oscillogram with a mathematical model, wherein the mathematical model is defined in terms of parameters with unknown values, the parameters indicating systolic pressure and diastolic pressure and parameters specifying a nonlinear blood volume-transmural pressure relationship of the artery underneath cuff of the automatic cuff device; estimating the parameters of the mathematical model by fitting the mathematical model to the oscillogram; constructing a blood volume waveform for the subject to within a scale factor, where the blood volume waveform is constructed from the oscillogram and the estimated mathematical model; determining a blood pressure waveform for the subject by applying the constructed blood volume waveform and the measured cuff pressure to the estimated nonlinear blood volume-transmural pressure relationship; and computing a mean blood pressure for the subject from the determined blood pressure waveform.

While estimating the parameters of the mathematical model, the parameters may be constrained such that derivative of the blood volume-transmural pressure relationship with respect to transmural pressure is maximum near zero and right skewed about the maximum. More specifically, parameters are constrained by setting a to near zero (e.g., 0-3 mmHg) and constraining value of b for each value of c such that derivative of the blood volume-transmural pressure relationship with respect to transmural pressure is right skewed by 30-50 percent about its peak.

The blood volume waveform may be constructed by subtracting a lower envelope of the cuff pressure oscillations as a function of cuff pressure from the cuff pressure oscillations as a function of cuff pressure to yield a waveform with positive amplitude oscillations; and summing the waveform with positive amplitude oscillations with the estimated nonlinear blood volume-transmural pressure relationship evaluated at estimated diastolic pressure.

The blood pressure waveform may be derived by finding the root of the estimated nonlinear blood volume-transmural pressure relationship at different points in time using the constructed blood volume waveform and measured cuff pressure.

In another aspect, a variant method is presented for determining blood pressure for a subject. The method includes: measuring cuff pressure using an automatic cuff device during a blood pressure measure of the subject; deriving an oscillogram from the measured cuff pressure, where the oscillogram is an amplitude of oscillations in measured cuff pressure as a function of the measured cuff pressure; representing the oscillogram with a mathematical model, wherein the mathematical model is defined in terms of parameters with unknown values, the parameters indicating systolic pressure and diastolic pressure and the parameters specifying a nonlinear blood volume-transmural pressure relationship of the artery underneath cuff of the automatic cuff device; constraining the parameters of the mathematical model such that the derivative of the blood volume-transmural pressure relationship with respect to transmural pressure is maximum near zero and right skewed about the maximum; and estimating the parameters of the mathematical model by fitting the mathematical model to the oscillogram.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 2:
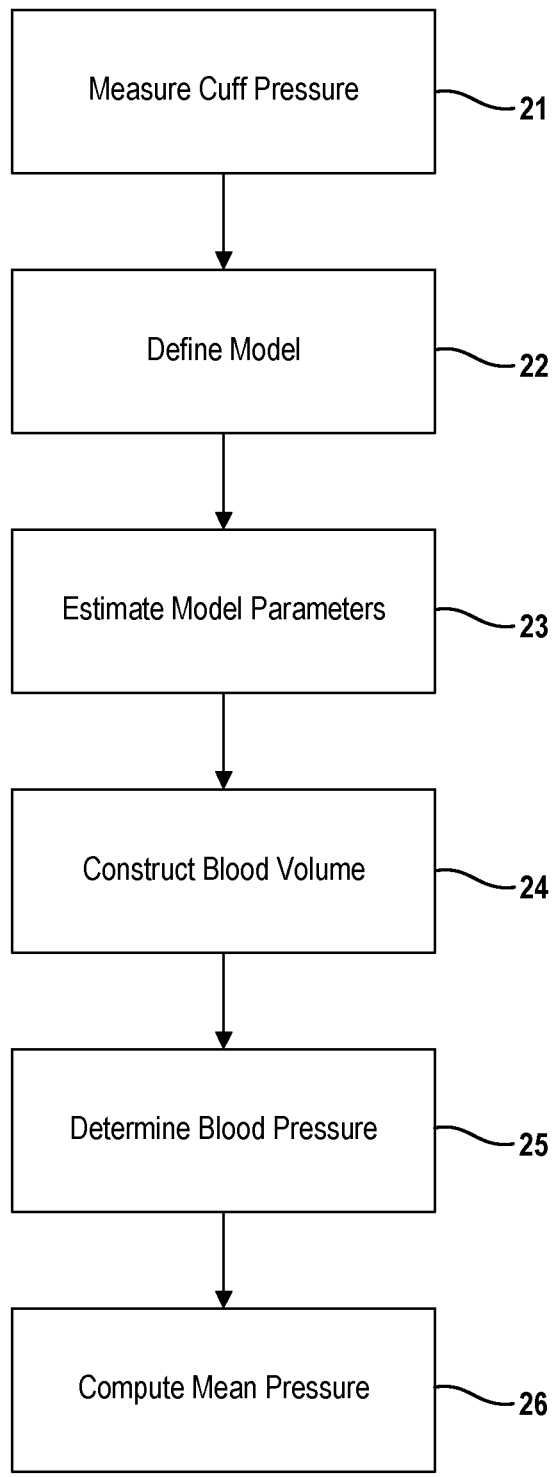
FIG. 2 is a flowchart for a patient-specific method for determining blood pressure.

FIG. 2 provides an overview of the proposed method for determining blood pressure for a subject. First, cuff pressure is measured at 21 during a blood pressure measure of the subject taken using, for example a sphygmomanometer or another type of automatic cuff device (e.g., having a strain gauge to measure pressure inside of the cuff). Automatic cuff devices act as both an actuator to alter the transmural pressure of the brachial artery via cuff inflation/deflation and a sensor to measure the pressure inside the cuff. The measured cuff pressure indicates the applied pressure and is superimposed with small oscillations representing the pulsatile blood volume in the artery. Since the volume-pressure relationship of the brachial artery is nonlinear, the amplitude of the cuff pressure oscillations varies with the applied cuff pressure. From the measured cuff pressure, an oscillogram is derived, where the oscillogram is the amplitude of the cuff pressure oscillations as a function of the measured cuff pressure.

A mathematical model representing the oscillogram can be defined at 21. More specifically, the oscillogram is represented using a parametric model. The parameters of the model represent systolic and diastolic blood pressures as well as define the nonlinear artery blood volume-transmural pressure relationship (as will be further described below).

Next, the parameters of the mathematical model are estimated at 23 by fitting the mathematical model to the oscillogram measured from the subject. The blood volume waveform is then constructed to within a scale factor at 24 using the measured oscillogram and the estimated mathematical model. A blood pressure waveform can be determined at 25 by applying the constructed blood volume waveform and measured cuff pressure waveform to the patient-specific artery blood volume-transmural pressure relationship (i.e., the estimated model). Lastly, a mean blood pressure for the subject is computed at 26 from the determined blood pressure waveform. Each of these steps is described in more detail below.

Figure 3:
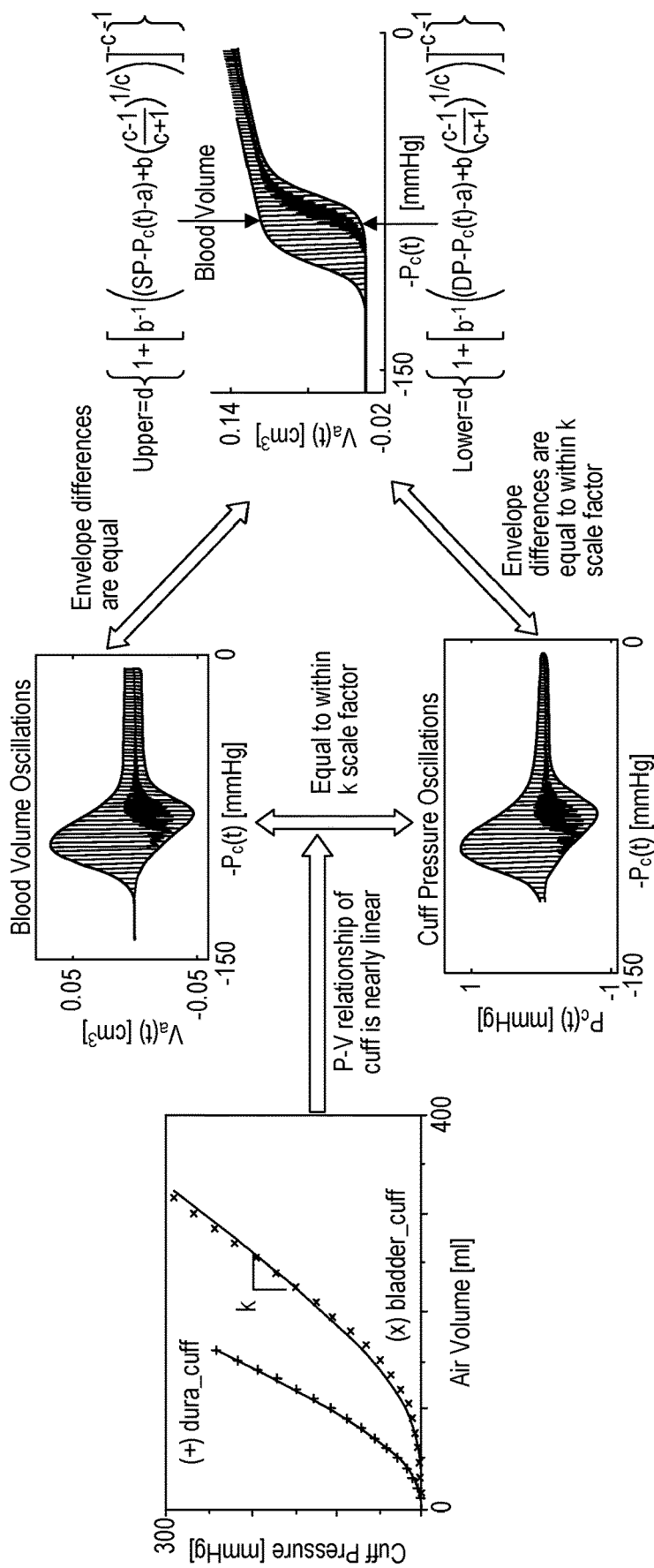
FIG. 3 is a diagram showing how to represent oscillation amplitude versus cuff pressure function using a parametric model.

With reference to FIG. 3, the oscillation amplitude versus cuff pressure function is represented using a parametric model accounting for the nonlinear artery blood volume-transmural pressure relationship. In an example embodiment, the mathematical model assumes a sigmoidal relationship between blood volume and transmural pressure as justified by experimental data and is, in particular, based on a left-shifted, Fisk cumulative probability distribution function as follows:

$$V_a(t) = d\left\{1 + \left[b^{-1}\left((P_a(t) - P_c(t) - a) + b\left(\frac{c-1}{c+1}\right)^{\frac{1}{c}}\right)\right]^{-c}\right\}^{-1} \quad (1)$$

where, t is time; $V_a(t)$ is the blood volume waveform; $P_a(t)$ is the BP waveform; $P_c(t)$ is the un-filtered cuff pressure waveform; and a, b, c, and d characterize the artery mechanics. In terms of the artery compliance curve, which is simply the derivative of Eq. (1) with respect to transmural pressure $[P_a(t)-P_c(t)]$, a (units of mmHg) denotes the transmural pressure at which the curve is maximal; b (units of mmHg) and c (unitless) together reflect the width of the curve and the degree of asymmetry about its maximum; and d (units of cm3) determines the amplitude of the curve. It is noted that Eq. (1) is only valid over the range specified by $(P_a(t)-P_c(t)-a)+b((c-1)/(c+1))^{1/c}>0$. Similar models based on the artery blood volume-transmural pressure relationship are also contemplated by this disclosure.

This proposed model can directly represent a blood volume versus cuff pressure function. That is, the upper and lower envelopes of the blood volume waveform as a function of cuff pressure may be represented with the above model by setting $P_a(t)$ to SP and DP, respectively (see right plot in FIG. 2 where the abscissae are specifically given by the negative of the un-filtered cuff pressure waveform). However, the blood volume waveform is not measured.

In order to apply the model to the measured cuff pressure waveform, two approximations are made. First, the difference in the upper and lower envelopes of the blood volume waveform as a function of negative cuff pressure is essentially equivalent to the difference in the upper and lower envelopes of the blood volume oscillations (i.e., the high-pass filtered blood volume waveform) as a function of negative cuff pressure (compare right and upper plots in FIG. 3). Second, the cuff pressure-air volume relationship of actual cuffs is nearly linear over a wide range (see left plot in FIG. 3). So, the unmeasured blood volume oscillations may be proportional to the measured cuff pressure oscillations (see upper and lower plots in FIG. 3) with a proportionality constant equal to k, which indicates the reciprocal of the compliance of the cuff. Note that these oscillations do not include the x-intercept of the cuff pressure-air volume relationship, as they are derived via high-pass filtering.

Putting the above model and approximations together, the measured oscillation amplitude versus cuff pressure function is precisely represented with the following model:

$$p_c^{oa}(t) = e\left\{1 + \left[b^{-1}\left((SP - P_c(t) - a) + b\left(\frac{c-1}{c+1}\right)^{\frac{1}{c}}\right)\right]^{-c}\right\}^{-1} - \quad (2)$$

$$e\left\{1 + \left[b^{-1}(DP - P_c(t) - a) + b\left(\frac{c-1}{c+1}\right)^{\frac{1}{c}}\right]^{-c}\right\}^{-1}$$

where $P_c^{oa}(t)$ is the cuff pressure oscillation amplitude waveform and $e = k \cdot d$ (units of mmHg). $P_c^{oa}(t)$ and $P_c(t)$ are derived from the measured oscillometric cuff pressure waveform and thus known; whereas, a, b, c, e, SP, and DP are patient-specific parameters and thus unknown.

The unknown parameters of the model are estimated by optimally matching both sides of Eq. (2) to each other, for example in the least squares sense. In particular, the following optimization problem is solved:

$$\min_{\{a,b,c,e,SP,DP\}} \sum_{t \in \text{Deflation Period}} \left[ p_c^{oa}(t) - \right. \quad (3)$$

$$e\left\{1 + \left[b^{-1}\left((SP - P_c(t) - a) + b\left(\frac{c-1}{c+1}\right)^{\frac{1}{c}}\right)\right]^{-c}\right\}^{-1} +$$

$$\left. e\left\{1 + \left[b^{-1}\left((DP - P_c(t) - a) + b\left(\frac{c-1}{c+1}\right)^{\frac{1}{c}}\right)\right]^{-c}\right\}^{-1} \right]^2$$

That is, the parameters of the mathematical model are estimated by fitting the mathematical relationship to oscillometric waveforms of the subject as measured by the automatic cuff device. While reference is made to a least squares method, it is readily understood that other methods, such as minimization of the absolute error, may be used to estimate the parameters of the mathematical model.

To improve accuracy, the estimation of the parameters of the mathematical model can be constrained within ranges of meaningful physiological values. For example, the transmural pressure at which the artery compliance curve is maximal (i.e., a) can be set at or near zero mmHg (e.g., 1-3 mmHg). Additionally or alternatively, b can be constrained for each value of c such that the compliance curve is right skewed by a fixed percent (e.g., 35-40%) about its peak. For example, referring to Equation 1, let x be Pa(t)–Pc(t) in Va(x). Then, (Va(a+20)–Va(a))/(Va(a)–Va(a–20))=1.4. This ensures 40% right-skewed asymmetry about the peak. Other constraints are also contemplated within the broader aspects of this disclosure.

Figure 4:
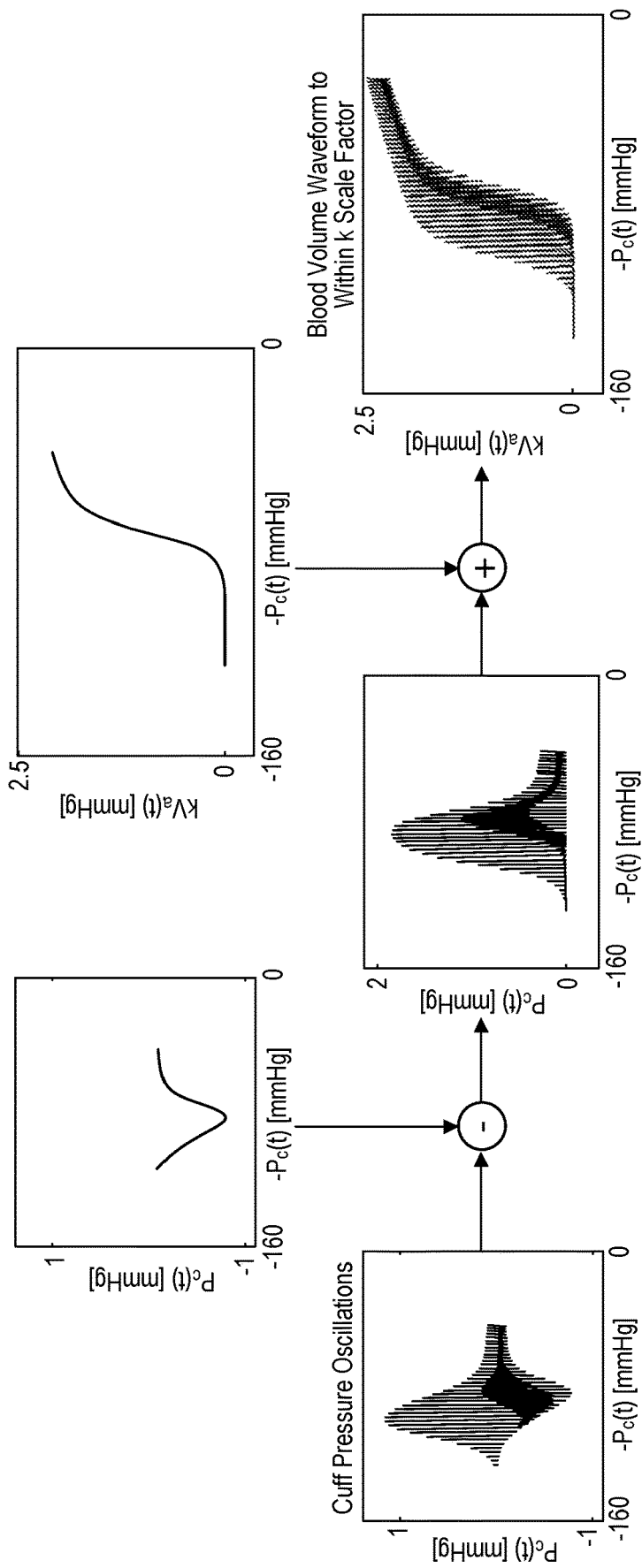
FIG. 4 is a diagram showing how to construct a blood volume waveform from oscillometric cuff pressure waveform.

Referring to FIG. 4, a scaled blood volume waveform [$k \cdot V_a(t)$] is constructed using the parameters of the estimated model. The basic idea is to construct (to within a scale factor) the right-most plot in FIG. 3, which indicates the blood volume waveform, by adding the cuff pressure oscillations to the lower envelope in this plot, which may be derived from the parameter estimates. More specifically, the lower envelope of the cuff pressure oscillations as a function of negative cuff pressure (second plot from left) is subtracted from the cuff pressure oscillations as a function of negative cuff pressure (left-most plot). The resulting waveform with positive amplitude oscillations is shown in the lower middle plot. The waveform with positive amplitude oscillations is then summed with a function defined by the estimated mathematical model at diastole. That is, the function defined by the model of Eq. (1) scaled by k with the parameter estimates for a, b, c, and e and $P_a(t)$ set to the DP estimate (second plot from right). The ordinates of the function resulting from these simple operations specify the scaled blood volume waveform (right-most plot). It is envisioned that the scaled blood volume waveform may also be analogously obtained from the upper envelope of the cuff pressure oscillations.

The blood pressure waveform is derived using the scaled blood volume waveform according to the model of Eq. (1) scaled by k. For each t, all quantities in this equation are known, except for $P_a(t)$. Hence, blood pressure is derived by finding the root of the equation at different points in time. Other techniques for deriving the blood pressure waveform from the blood volume waveform also fall within the scope of this disclosure.

Finally, a mean blood pressure for the subject is computed from the determined blood pressure waveform. For example, the time average of the constructed blood pressure waveform is computed so as to yield an estimate for mean pressure.

To assess the patient-specific method, a total of 158 human subjects were studied at Taipei Veterans General Hospital (Taiwan). All procedures were approved by the Institutional Review Board of the hospital and adhered to the principles of the Declaration of Helsinki. Written, informed consent was obtained from all subjects prior to study.

Amongst the subjects, 138 were adult patients admitted for diagnostic cardiac catheterization. Briefly, all patients had normal sinus rhythm and inter-arm BP differences of no more than 3 mmHg. A micromanometer-tipped catheter (SPC-320, Millar Instruments, USA) was inserted into a brachial artery to measure the gold standard reference BP waveform. An inflatable cuff of an office oscillometric device (WatchBP Office, Microlife AG, Switzerland or VP-1000, Omron Colin, Japan) was placed over the other brachial artery to measure the raw cuff pressure waveform for analysis and to obtain the BP estimates of the device. The waveforms were simultaneously recorded during baseline and/or sublingual nitroglycerin administration. When the Microlife device was used, two cuff pressure waveforms were recorded per condition via repeated cuff inflation/deflation cycles.

The remaining 20 subjects were normal adults. The inflatable cuff of the Microlife device was placed over a brachial artery to again measure the cuff pressure waveform for analysis and obtain the BP estimates of the device. Using a three-way stopcock, the same cuff was interfaced to a mercury sphygmomanometer to simultaneously obtain reference SP and DP from the same arm via auscultation. The auscultation measurements were performed strictly according to AHA guidelines. Two pairs of cuff pressure waveforms and auscultation measurements were recorded via repeated cuff inflation/deflation cycles.

The cuff pressure waveforms for analysis and invasive reference BP waveforms were visually screened for substantial artifact due to motion or otherwise. All waveforms with such artifact were excluded from subsequent analysis to benchmark method performance. A total of 315 pairs of cuff pressure waveforms and reference BP measurements from 145 patients and normal subjects remained for analysis.

The measurement pairs from 57 of the patients were utilized as training data to refine the method, while the remaining data from 88 patients and normal subjects were utilized as testing data to evaluate the method. Note that while patient-specific methods do not require training data in theory, all methods need such data in practice to define their user-selected variables. Table 1 summarizes the measurement and subject characteristics of the training and testing datasets for analysis. Table 2 shows the average, standard deviation, and range of reference SP, MP, DP, and PP during baseline and nitroglycerin administration for the patients and normal subjects in the testing dataset. Hence, the BP levels varied widely, with PP and SP ranging from normal levels to high levels due to large artery stiffening. The corresponding statistics for the training dataset, which are reported elsewhere, indicated a fairly similar BP range.

TABLE I

Measurement and Subject Characteristics

|  | Training Data | | Testing Data | | |
| --- | --- | --- | --- | --- | --- |
|  | Cohort 1 | Cohort 2 | Cohort 1 | Cohort 2 | Cohort 3 |
| Measurement Characteristics | | | | | |
| Device | Omron | Microlife | Omron | Microlife | Microlife |
| Reference | Invasive | Invasive | Invasive | Invasive | Auscultation |
| # of Subjects | 20 | 37 | 58 | 11 | 19 |
| # of Baseline Measurements | 20 | 37 | 36 | 11 | 19 |
| # of Nitroglycerin Measurements | 8 | 36 | 32 | 11 | 0 |
| # of Repeated Measurements | 0 | 73 | 0 | 16 | 16 |
| Total # of Measurements | 28 | 146 | 68 | 38 | 35 |
| Subject Characteristics | | | | | |
| Type | Cardiac Catheterization | | | | Normal |
| Age [years] | 65.1 ± 15.4 | 65.2 ± 12.3 | 59.8 ± 15.0 | 69.0 ± 12.4 | 34.0 ± 9.4 |
| Weight [kg] | 64.5 ± 12.4 | 74.6 ± 13.4 | 70.12 ± 11.5 | 68.9 ± 14.2 | 60.4 ± 15.8 |
| Height [cm] | 164.0 ± 6.4 | 163.6 ± 8.0 | 161.6 ± 7.8 | 162.2 ± 10.4 | 164.2 ± 9.3 |
| Waist circumference [cm] | 84.6 ± 11.4 | 90.0 ± 12.3 | 91.8 ± 9.5 | 97.2 ± 11.9 | 75.8 ± 11.2 |
| Men [%] | 85 | 75.7 | 74.1 | 72.7 | 36.8 |
| Smoking [%] | 35 | 18.9 | 20.7 | 27.3 | N/A |
| Clinical diagnosis [%] | | | | | |
| Hypertension | 65 | 59.5 | 56.9 | 90.9 | N/A |
| Type 2 Diabetes Mellitus | 20 | 29.7 | 31 | 54.5 | N/A |
| Dyslipidemia | 45 | 37.8 | 41.4 | 36.4 | N/A |
| Coronary Artery Disease | 40 | 59.5 | 56.9 | 63.6 | N/A |
| Chronic Renal Failure | 5 | 2.7 | 3.4 | 18.2 | N/A |
| Medications [%] | | | | | |
| α-Blockers | 20 | 13.5 | 12.1 | 27.3 | N/A |
| β-Blockers | 30 | 43.2 | 37.9 | 63.6 | N/A |
| Calcium Channel Blockers | 25 | 48.6 | 41.4 | 27.3 | N/A |
| Diuretics | 20 | 18.9 | 20.7 | 36.4 | N/A |
| Antiplatelet Agents | 65 | 86.5 | 70.7 | 81.8 | N/A |

TABLE II

Reference Blood Pressure (BP) Levels in the Testing Data

| Reference BP | Condition | SP [mmHg] | MP [mmHg] | DP [mmHg] | PP [mmHg] |
| --- | --- | --- | --- | --- | --- |
| Invasive | Baseline | 136 ± 20 (109-192) | 97 ± 13 (76-127) | 72 ± 11 (46-95) | 64 ± 16 (45-107) |
|  | Nitroglycerin | 130 ± 18 (99-169) | 92 ± 12 (72-115) | 70 ± 11 (46-70) | 60 ± 18 (31-102) |
| Auscultation | Baseline | 105 ± 11 (88-130) | N/A | 71 ± 10 (54-88) | 34 ± 9 (21-54) |

First, the training dataset was analyzed. The requisite oscillogram for BP estimation was constructed from each cuff pressure waveform as described previously.

The user-selected variables of the patient-specific method were determined by maximizing the agreement between its BP estimates and the reference BP values while minimizing the number of parameters for estimation in order to enhance robustness. The resulting user-selected variables included fixing the a parameter, which indicates the peak position of the brachial artery compliance curve, to 1.5 immHg and the b parameter for each value of the c parameter such that the compliance curve was right-skewed by 40% about its maximum. Note that these parameter settings are buttressed by directly measured compliance curves. Hence, the optimized patient-specific method estimated four parameters [SP, DP, c, e] from the oscillogram.

A fixed-ratio method was likewise developed using the training dataset by maximizing the agreement between its BP estimates from the same oscillograms and the reference BP values. The resulting fixed ratio values were 0.57 for SP and 0.75 for DP.

Then, the testing dataset was analyzed. The patient-specific and fixed-ratio methods were applied to oscillograms likewise constructed from the cuff pressure waveforms. The BP estimates of these methods and the office device were compared for accuracy and repeatability.

For accuracy, note that the testing dataset included reference BP via brachial artery catheterization or auscultation (see Table 1). Further note that the patient-specific and fixed-ratio methods were trained based on the former reference method (see Table 1), whereas the office device was likely developed based on the latter reference method. Since there are systematic differences between the two reference methods (i.e., invasive SP and DP are a few mmHg higher and lower than auscultation SP and DP, respectively), bias accuracy could not be fairly quantified and compared. To quantify precision accuracy, the errors between the SP, MP, DP, and PP estimates and the reference BP values were computed. The bias component of each of these errors for each method in each of the three cohorts in the testing dataset (see Table 1) was then removed. The resulting precision errors were divided into two groups: normal PP (reference PP<50 mmHg) and high PP (reference PP>50 mmHg). Note that a 50 mmHg threshold was chosen so as to arrive at groups of approximately equal size. In the case of repeated measurement pairs, only the first measurement pair was included in the groups. The root-mean-square (RMS) of the errors and percentage of large errors (i.e., percent of absolute errors>10 and 15 mmHg) in each PP group were then computed. Finally, to compare precision accuracy, the Pittman-Morgan test was applied to the RMS of the errors (which were nearly void of a bias component) of pairs of methods in each PP group. A p<0.0167 (=0.05/3) was considered significant based on Bonferroni correction for pairwise comparison of three methods.

For repeatability, the mean and standard deviation of the differences between each of the repeated estimates of SP, MP, DP, and PP of each method were computed. The paired t-test and Pittman-Morgan test were then applied to compare the resulting bias and precision of pairs of methods, respectively. A p<0.0167 was likewise considered significant.

Figure 5:
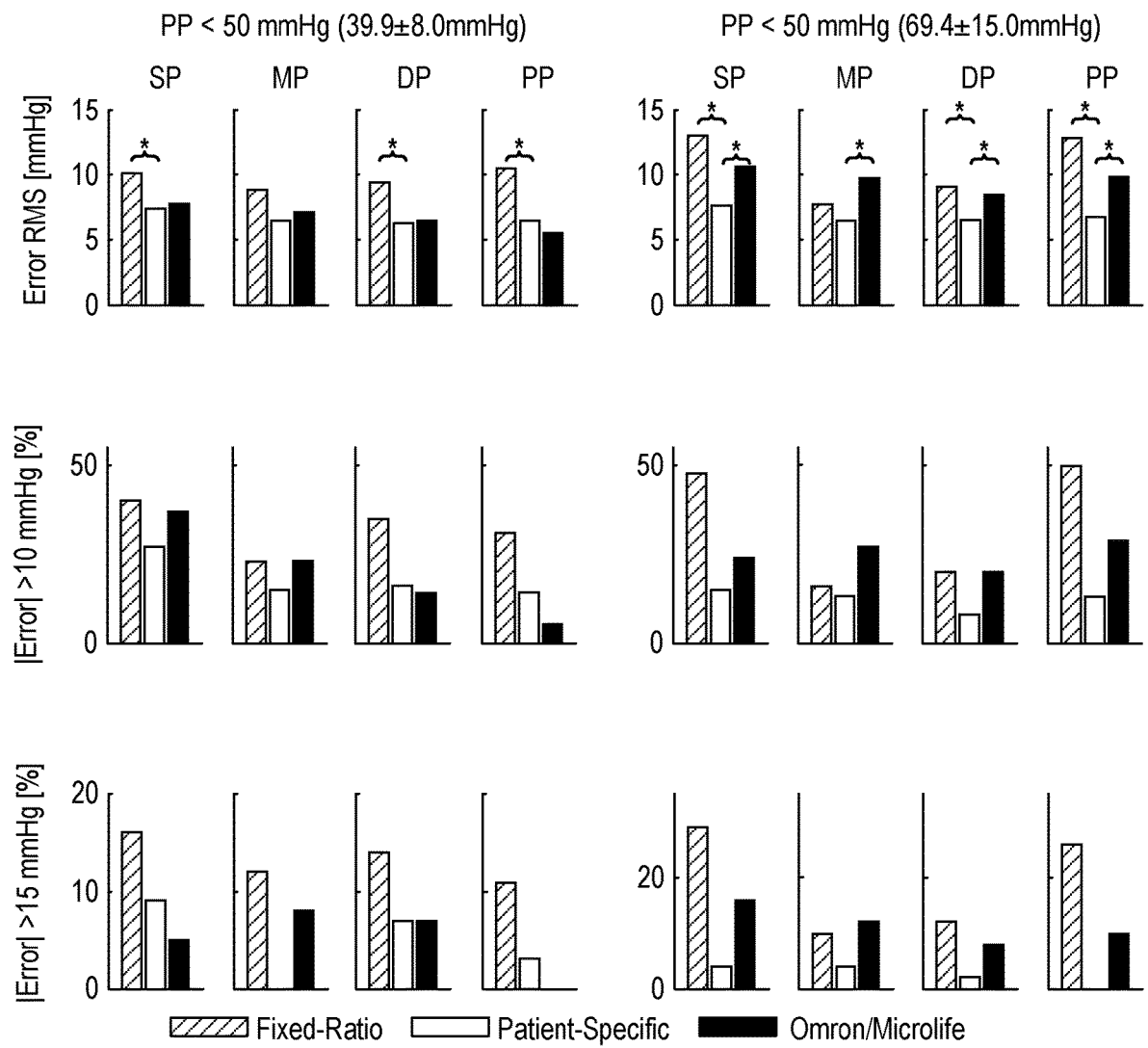
FIG. 5 is bar graphs showing blood pressure precision error metrics in the normal and high reference pulse pressure groups for the patient-specific method and two available methods.

FIG. 5 summarizes the SP, MP, DP, and PP precision accuracy results for the patient-specific method, fixed-ratio method, and Omron/Microlife device in the normal PP and high PP groups of the testing dataset. These results were obtained from 88 subjects wherein the normal PP and high PP groups constituted 42 and 58% of the data, respectively.

Figure 7:
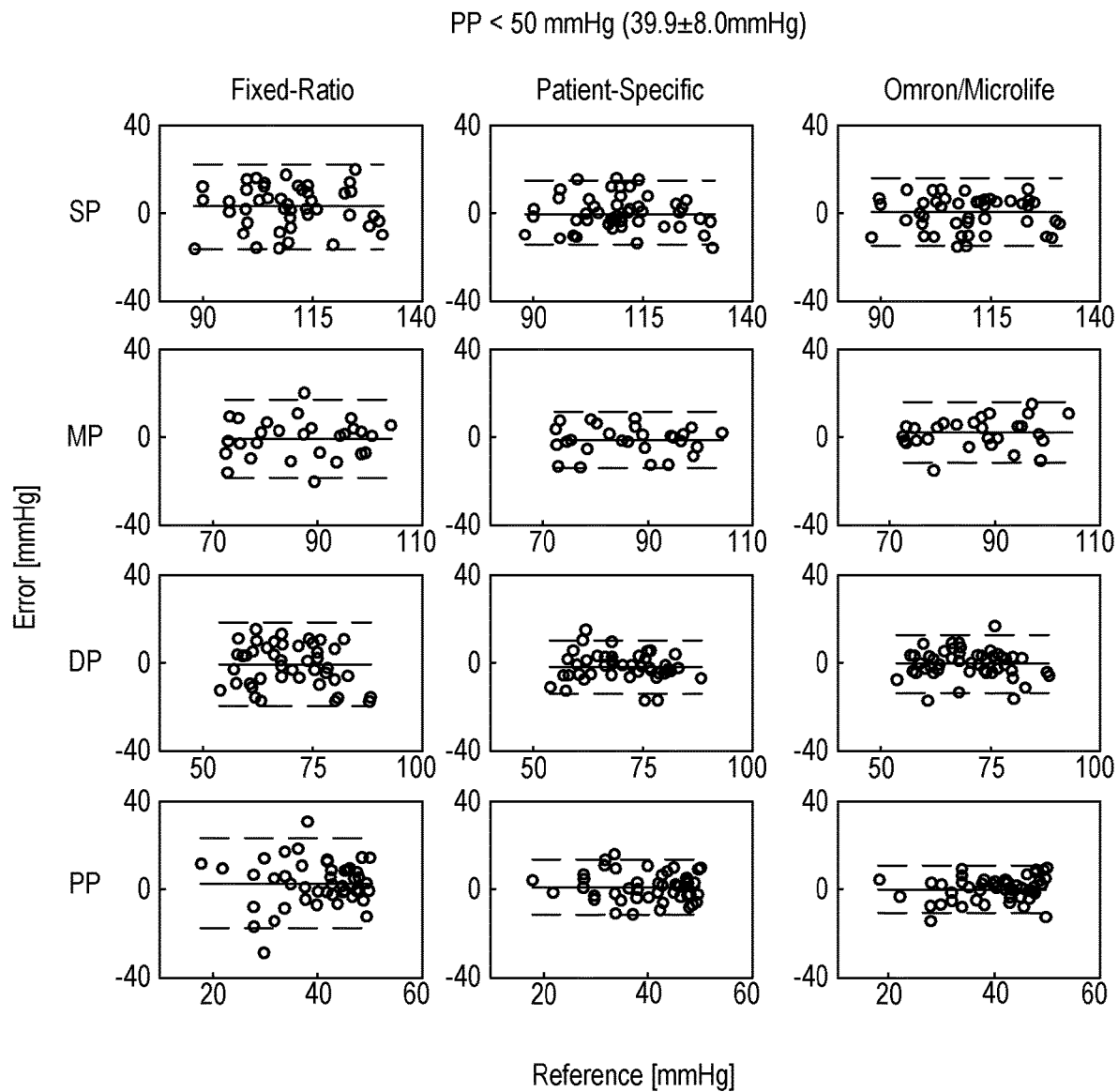
FIG. 7 are Bland-Altman plots (mean±1.96·SD) of the precision errors in the normal pulse pressure group for the patient-specific method in comparison to two existing methods.
Figure 8:
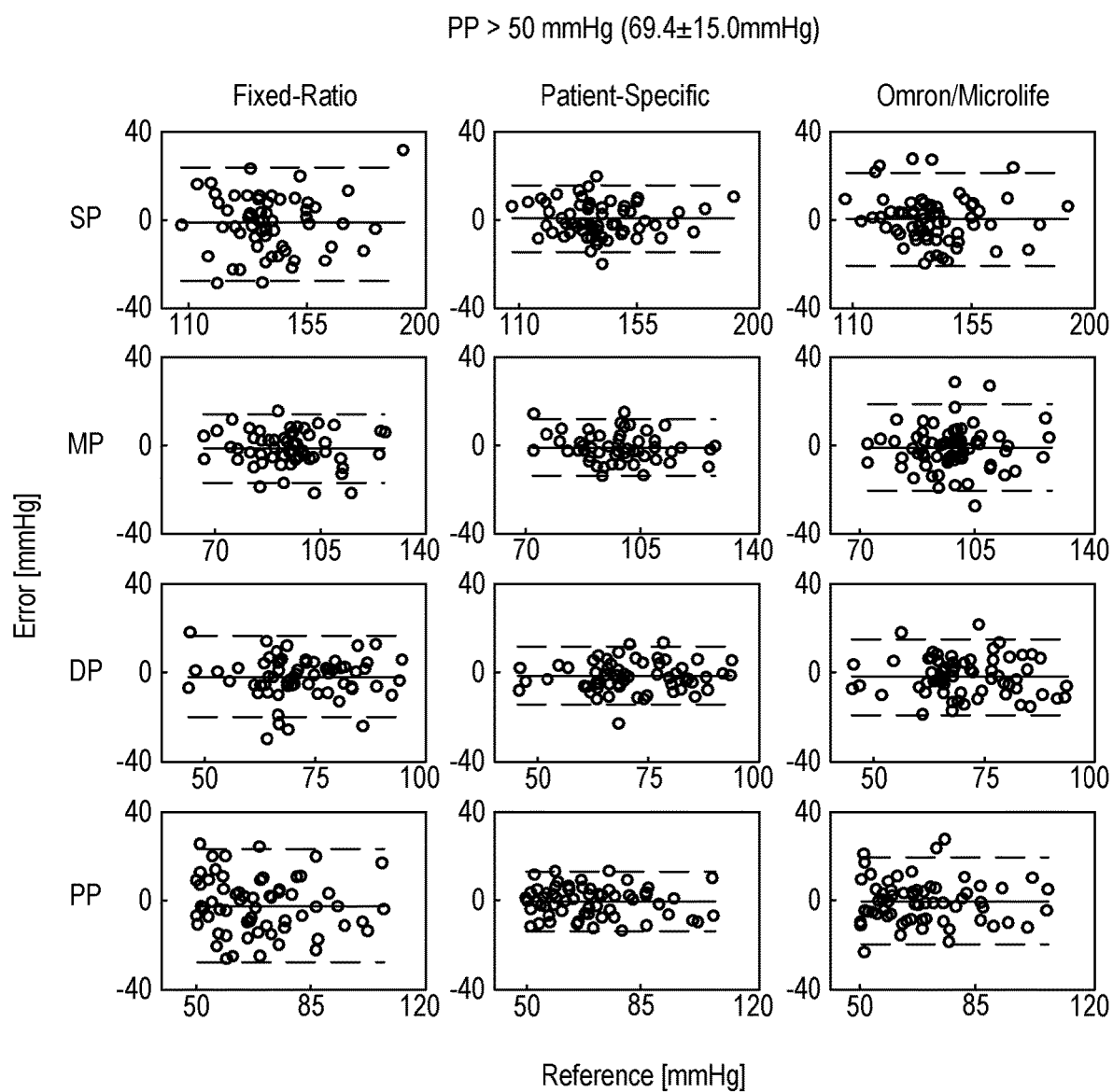
FIG. 8 are Bland-Altman plots (mean±1.96·SD) of the precision errors in the high pulse pressure group for the patient-specific method in comparison to two existing methods.

The mean±SD of PP was 39.9±8.0 mmHg in the normal PP group and 69.4±15.0 mmHg in the high PP group. The RMS errors of the patient-specific method ranged from 6.3 to 7.6 mmHg over both PP groups, and its percentages of large errors were fairly similar between the groups. Hence, the patient-specific method was able to maintain the precision accuracy over a wide PP range. Furthermore, the precision errors of this method were significantly lower (or not different) relative to the fixed-ratio method in both PP groups. In particular, the RMS errors for SP, DP, and PP of the patient-specific method were, on average, 36% smaller than those of the fixed-ratio method, while the absolute precision errors exceeding 10/15 mmHg of the new method were, on average, 50/75% less than the standard method. More notably, the precision errors of the patient-specific method were significantly lower relative to the widely employed Omron/Microlife device in the high PP group while being similar in the normal PP group. Specifically, in the high PP group, the RMS errors for all BP levels of the patient-specific method were, on average, 29% smaller than those of the Omron/Microlife device, while the absolute precision errors exceeding 10/15 mmHg of the new method were, on average, 51/79% less than the office device. Hence, the patient-specific method was able to reduce the number of large precision errors and improve the precision accuracy, especially over the high PP range. FIGS. 7 and 8 shows Bland-Altman plots for visual assessment of the precision errors.

Figure 6:
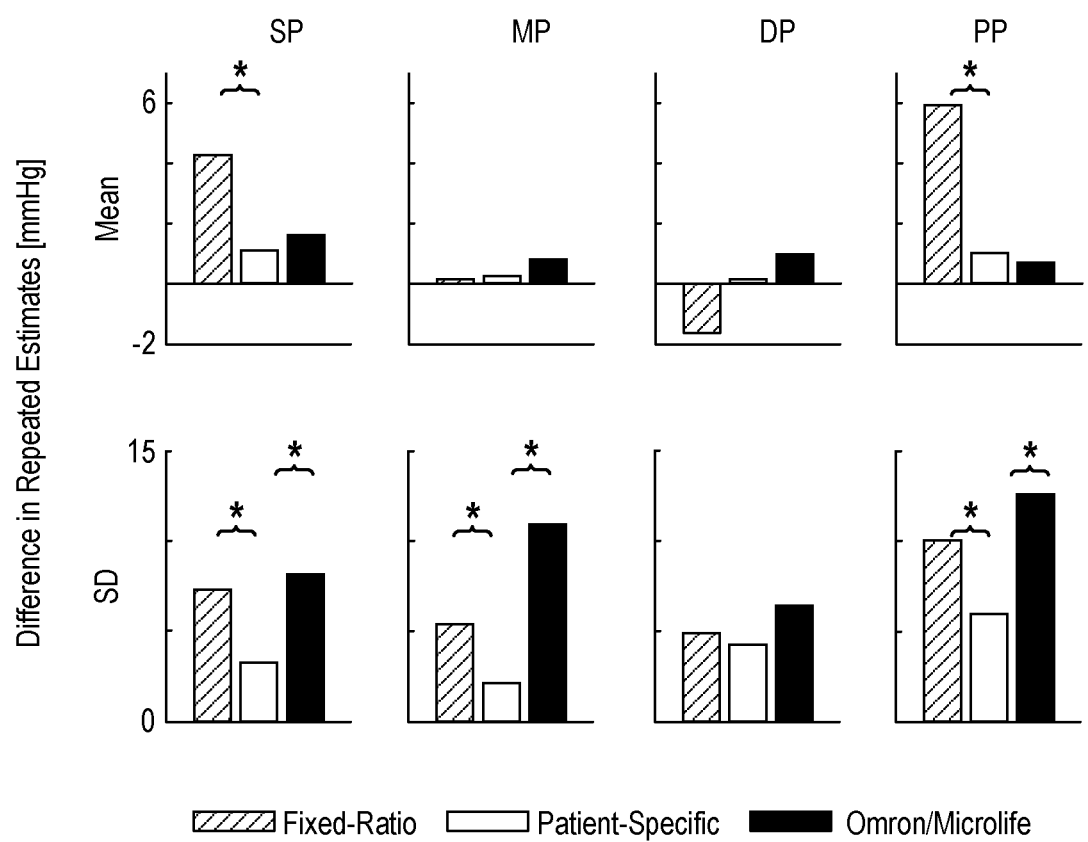
FIG. 6 is bar graphs showing blood pressure repeatability metrics for the patient-specific method and two available methods.
Figure 9:
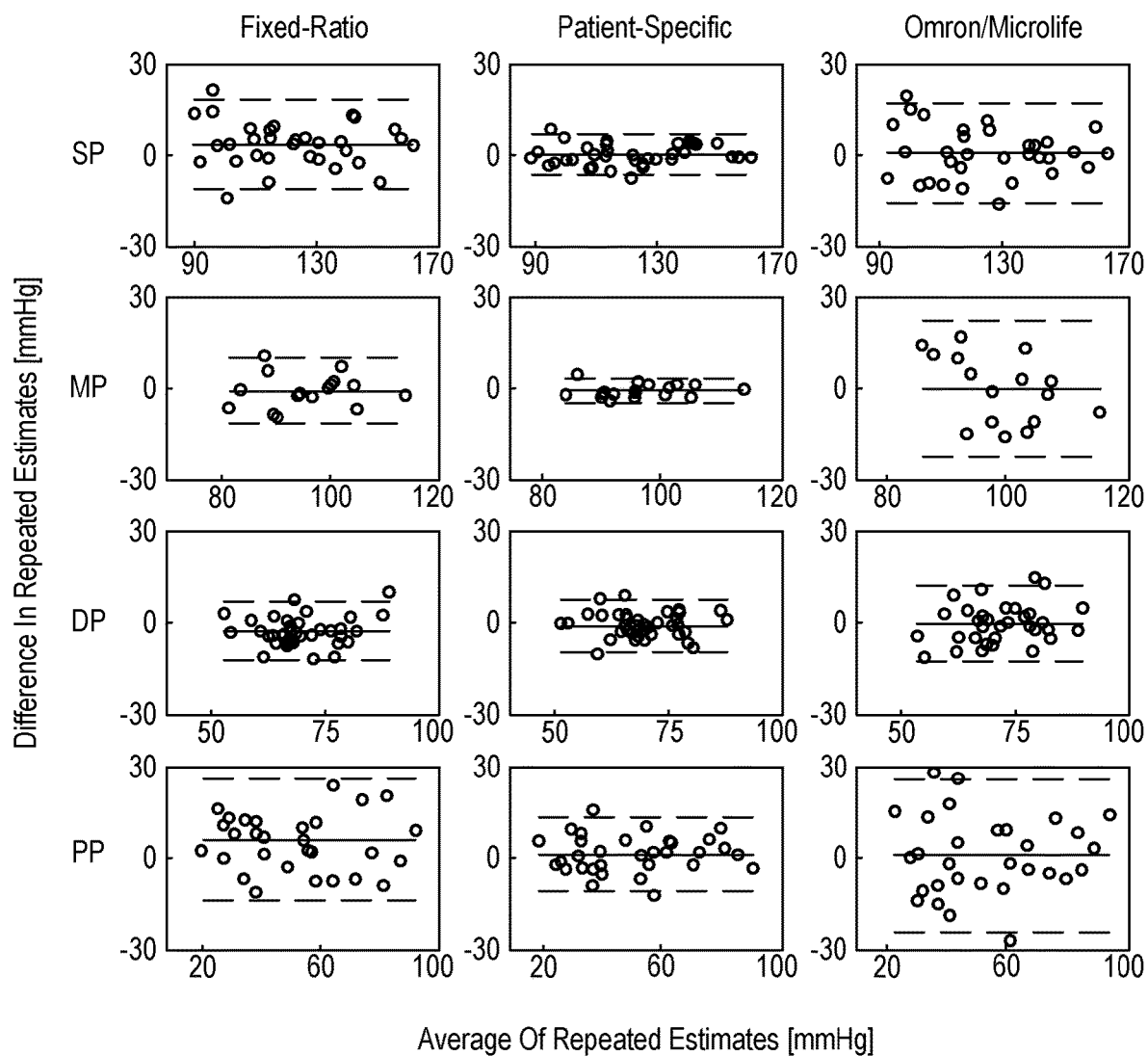
FIG. 9 are Bland-Altman plots (mean±1.96·SD) of the differences in repeated estimates for the patient-specific method in comparison to two existing methods.

FIG. 6 summarizes the SP, MP, DP, and PP repeatability results for the three methods in the testing dataset. These results were obtained from 32 subjects for SP, DP, and PP and 16 subjects for MP. The bias and precision of the differences in repeated estimates for all BP levels of the patient-specific method ranged from 0.1 to 1.1 mmHg and 2.1 to 5.9 mmHg, respectively. These values were significantly lower (or not different) relative to the other methods. In particular, the bias of the differences in repeated estimates for SP and PP of the patient-specific method were, on average, 79% smaller than those of the fixed-ratio method, while the precision of the differences in repeated estimates for SP, MP, and PP of the new method were, on average, 53% smaller than those of the standard method and 64% smaller than those of the Microlife device. Hence, the patient-specific method was able to improve BP measurement repeatability. FIG. 9 shows Bland-Altman plots for visual assessment of the differences.

Secondary results (which are not shown) were as follows. Firstly, and as alluded to earlier, the bias accuracy for the SP and DP estimates of the patient-specific method tended to be superior relative to the Omron/Microlife device when invasive BP was the reference (bias error of −2.4 vs. −5.4 mmHg for SP and −0.1 vs. 1.5 mmHg for DP; p=NS) but tended to be worse compared to the office device when auscultation BP was the reference (4.0 vs. 2.4 mmHg for SP and −6.6 vs. −3.9 mmHg for DP; p=NS). However, the precision accuracy of the patient-specific method was similar relative to the office device when auscultation BP was the reference (precision error of 5.3 vs. 6.4 mmHg for SP and 5.2 vs. 5.1 mmHg for DP). Further, the c and e parameter estimates of the patient-specific method were 5.2±0.7 (mean±SD) unitless and 8.2±1.4 mmHg during baseline and 5.9±1.0 unitless and 8.9±1.4 mmHg during nitroglycerin administration, respectively (p 0.013 via t-tests). Increases in the c and e parameters both correspond to enhanced brachial artery compliance, so the patient-specific method was able to correctly track the drug-induced compliance changes. Finally, and perhaps as a result, the precision accuracy of the patient-specific method tended to be less impacted by nitroglycerin administration than the Omron/Microlife device (average difference in RMS error from baseline to nitroglycerin administration of −0.98 mmHg vs. −1.95 mmHg).

Figure 1:
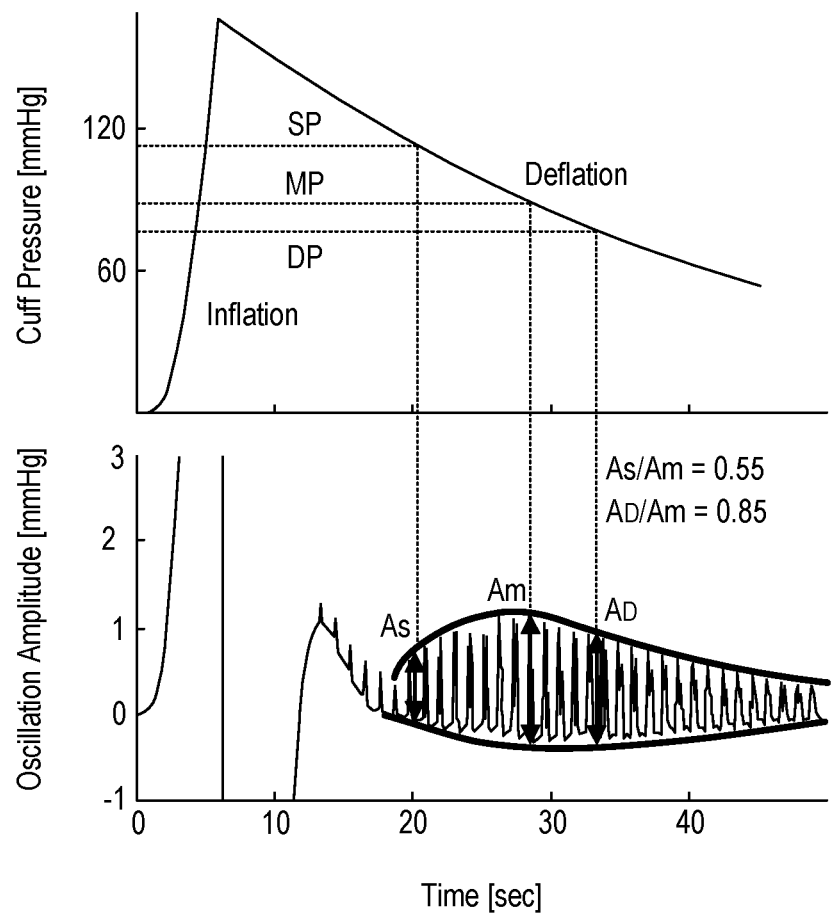
FIG. 1 is a diagram illustrating the conventional fixed-ratio method for estimating systolic blood pressure (SP), diastolic blood pressure (DP) and mean blood pressure (MP)

Most automatic cuff BP measurement devices employ population average methods to estimate BP from an oscillogram and may thus be accurate only over a limited BP range. A patient-specific method is proposed to estimate BP from the oscillogram by leveraging a physiologic model in conjunction with model fitting (see FIG. 1). In this way, the routinely used devices may not only maintain accuracy over a wider BP range but also be less sensitive to common physiologic deviations in the oscillogram and thus more repeatable. In the pivotal test, the method was refined and compared to existing methods for accuracy and repeatability in 145 human subjects with normal PP levels and high PP levels induced by large artery stiffening (see Tables 1 and 2).

The patient-specific method achieved BP errors reflecting precision accuracy that ranged from 6.3 to 7.6 mmHg (see FIG. 5). Hence, the method maintained the precision accuracy over both the normal and high PP ranges. Further, this level of precision accuracy was within the Association for the Advancement of Medical Instrumentation (AAMI) precision limits of 8 mmHg. However, the method did not meet the AAMI standard, because an AAMI data collection protocol was not employed.

The patient-specific method was compared to both the standard fixed-ratio method, which was developed using the same training dataset as the new method, and a currently used office device (Omron or Microlife). Overall, the office device attained greater precision accuracy than the fixed-ratio method (see FIG. 5), thereby suggesting that the device estimates BP based on other useful features in the oscillogram in addition to, or instead of, amplitude ratios. However, the level of precision accuracy of the office device was not within 8 mmHg for the high PP range. Compared to this device, the patient-specific method revealed significantly lower precision errors for all BP levels in the high PP range (by 29 to 79% on average) while showing similar precision errors in the normal PP range (see FIGS. 5, 7 and 8).

The reference method was either auscultation BP or invasive BP in the normal PP range but almost exclusively invasive BP in the high PP range. The well-known auscultatory gap is strongly related to carotid artery stiffening and aging and thus high PP. Perhaps as a result, the ability of auscultation to stratify risk for stroke and heart disease diminishes with aging. Since auscultation BP was not utilized as the reference in the high PP range, the improvement in precision accuracy attained by the patient-specific method here may be particularly significant. The improved precision accuracy with respect to invasive BP could also be significant in terms of monitoring central BP, which may offer superior cardiovascular risk stratification to brachial BP. That is, a major source of error of non-invasive measurements of central BP is the discrepancy between the BP estimates of current oscillometric devices, which are used to calibrate the tonometry waveforms, and invasive brachial BP. Hence, the patient-specific method may be able to enhance the accuracy of non-invasive central BP monitoring.

The bias accuracy of the methods could not be fairly assessed and compared due to the systematic differences in the two reference methods employed for training as well as testing them. While the inability to address bias accuracy represents the main limitation of the pivotal test, precision accuracy may be much more important anyhow. For example, the bias accuracy of the patient-specific method, which was developed using the invasive BP reference, could easily be corrected for an auscultation BP reference by subtracting and adding a constant (e.g., 3-4 mmHg) to its SP and DP estimates, respectively.

The patient-specific method also achieved a bias and precision of the differences in repeated BP estimates that ranged from 0.1 to 1.1 mmHg and 2.1 to 5.9 mmHg, respectively (see FIG. 6). This level of repeatability was within the AHA recommended limits of 5 mmHg for SP, MP, and DP and near these limits for PP.

While the office device was more accurate than the fixed-ratio method, the standard method appeared more repeatable (see FIG. 9). However, the level of repeatability of the fixed-ratio method was not close to the AHA limits for SP and PP (see FIG. 6). Compared to this method, the patient-specific method revealed significantly lower bias of the differences in repeated SP and DP estimates (by 79% on average) and precision of the differences in repeated SP, MP, and PP estimates (by 53% on average) (see FIGS. 6 and 9).

In sum, the patient-specific method afforded superior precision accuracy, especially in the high PP range wherein gold standard invasive BP served as the reference, and repeatability compared to widely used, population-based methods. Hence, the new method could improve cardiovascular risk stratification in the elderly and other patients with large artery stiffening while limiting the number of required cuff inflations/deflations per BP measurement.

Hypertension detection and control currently represent a major healthcare problem around the world, especially in low resource settings. Effective BP measurement technology is essential to alleviate this problem. Amongst the available technologies, oscillometry offers a number of advantages. In particular, it is non-invasive (unlike catheterization), easy-to-use (unlike manual auscultation or tonometry), inexpensive (unlike volume clamping), unaffected by the auscultatory gap and terminal digit bias (unlike manual auscultation), less sensitive to cuff position and ambient sound (compared to automatic auscultation), environmentally safe (unlike mercury manometers), and more convenient in terms of maintenance (compared to aneroid manometers). However, the disadvantage of oscillometry is that it is not as accurate as other technologies (catheterization and manual auscultation). The reason is that BP is estimated from the oscillogram using population average methods. The patient-specific method was evaluated for estimating BP from a standard oscillogram. The new method showed significantly improved accuracy over a wide PP range as well as repeatability compared to the standard BP estimation method and widely used office devices. With further testing, the patient-specific method could possibly facilitate the management of hypertension by affording more accurate automatic cuff blood pressure measurement in patients with large artery stiffening while limiting the number of required cuff inflations/deflations per measurement.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware or hardware, and when embodied in software, could be downloaded to reside on and be operated from different platforms used by real time network operating systems.

Figure 10:
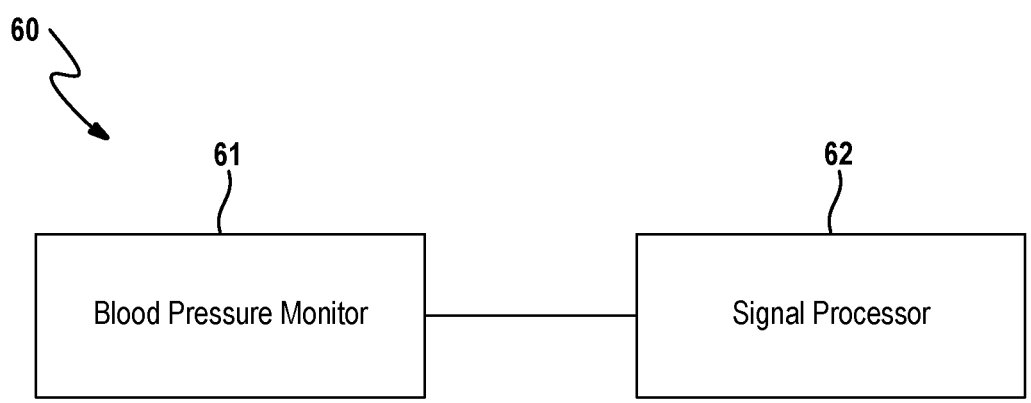
FIG. 10 is a block diagram of an apparatus for determining blood pressure in accordance with the patient-specific methods.

With reference to FIG. 10, the present disclosure also relates to an apparatus 60 for determining blood pressure in accordance with patient-specific methods set forth above. The apparatus 60 is comprised of a blood pressure monitor 61 and a signal processor 62. During operation, the blood pressure monitor 61 is configured to measure the oscillometric cuff pressure waveform of the subject; whereas, the signal processor 62 implements the steps of estimating the parameters of the mathematical model including systolic and diastolic blood pressures, constructing a blood volume waveform for the subject to within a scale factor, determining a blood pressure waveform for the subject, and computing a mean blood pressure for the subject. The mathematical model may be stored in a non-transitory computer memory associated with the signal processor 62.

In one embodiment, the blood pressure monitor 61 is further defined as a sphygmomanometer or another automatic cuff device. The signal processor may be specially constructed for the required purposes, or it may comprise a general-purpose computer selectively activated or reconfigured by a computer program stored on a computer readable medium that can be accessed by the computer. Such a computer program may be stored in a tangible computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and operations presented herein are not inherently related to any particular computer or other apparatus. Various general-purpose systems may also be used with programs in accordance with the teachings herein, or it may prove convenient to construct more specialized apparatuses to perform the required method steps. The required structure for a variety of these systems will be apparent to those of skill in the art, along with equivalent variations. In addition, the present disclosure is not described with reference to any particular programming language. It is appreciated that a variety of programming languages may be used to implement the teachings of the present disclosure as described herein.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for determining mean blood pressure fora subject, comprising:
   measuring cuff pressure using an automatic cuff device during a blood pressure measure of the subject;
   deriving an oscillogram from the measured cuff pressure, where the oscillogram is an amplitude of oscillations in the measured cuff pressure as a function of the measured cuff pressure;
   representing the oscillogram with a mathematical model, wherein the mathematical model is defined in terms of parameters with unknown values, the parameters indicating systolic pressure and diastolic pressure and specifying a nonlinear blood volume-transmural pressure relationship of the artery underneath a cuff of the automatic cuff device;
   estimating the parameters of the mathematical model by fitting the mathematical model to the oscillogram while constraining the derivative of the blood volume-transmural pressure relationship in the mathematical model, with respect to transmural pressure, with a maximum near zero and right skewed about the maximum;
   constructing a blood volume waveform for the subject to within a scale factor, where the blood volume waveform is constructed from the oscillogram and the estimated mathematical model;
   determining a blood pressure waveform for the subject by applying the constructed blood volume waveform and the measured cuff pressure to the estimated nonlinear blood volume-transmural pressure relationship; and
   computing a mean blood pressure for the subject from the determined blood pressure waveform.

2. The method of claim 1 wherein the mathematical model is further defined as $$p_c^{oa}(t) = e\left\{1 + \left[b^{-1}\left([(SP - P_c(t) - a) + b]\left(\frac{c-1}{c+1}\right)^{\frac{1}{c}}\right)\right]^{-c}\right\}^{-1} - e\left\{1 + \left[b^{-1}(DP - P_c(t) - a) + b\left(\frac{c-1}{c+1}\right)^{\frac{1}{c}}\right]^{-c}\right\}^{-1}$$

where t is time; $P_c^{oa}(t)$ is amplitude of oscillations in the measured cuff pressure; $P_c(t)$ is the measure cuff pressure; SP is systolic pressure; DP is diastolic pressure; and a, b, c, and e characterize the nonlinear blood volume-transmural pressure relationship of the subject.

3. The method of claim 2 further comprises estimating the parameters of the mathematical relationship by least squares fitting of both sides of the equation to each other.

4. The method of claim 2 further comprises estimating the parameters of the mathematical model by setting a to 0-3 mmHg and constraining value of b for each value of c such that derivative of the blood volume-transmural pressure relationship with respect to transmural pressure is right skewed by 30-50 percent about its peak.

5. The method of claim 1 wherein constructing a blood volume waveform further comprises:
   subtracting a lower envelope of the cuff pressure oscillations as a function of cuff pressure from the cuff pressure oscillations as a function of cuff pressure to yield a waveform with positive amplitude oscillations; and summing the waveform with positive amplitude oscillations with the estimated nonlinear blood volume-transmural pressure relationship evaluated at estimated diastolic pressure.

6. The method of claim 1 wherein determining a blood pressure waveform for the subject further comprises deriving the blood pressure waveform by finding the root of the estimated nonlinear blood volume-transmural pressure relationship at different points in time using the constructed blood volume waveform and measured cuff pressure.

7. The method of claim 1 further comprises computing the mean blood pressure by taking a time average of the determined blood pressure waveform.

8. The method of claim 1 wherein the automatic cuff device is further defined as a sphygmomanometer.

9. An apparatus for determining blood pressure for a subject, comprising:
 a blood pressure monitor configured to measure an oscillometric waveform of cuff pressure during a measure of blood pressure;
 a non-transitory data store for storing a mathematical model, where the mathematical model is defined in terms of parameters with unknown values, the parameters indicating systolic pressure and diastolic pressure and specifying a nonlinear blood volume-transmural pressure relationship of the artery underneath a cuff of the blood pressure monitor; and
 a signal processor configured to receive the oscillometric waveform of cuff pressure and from the blood pressure monitor, derive an oscillogram from the oscillometric waveform and estimate the parameters of the mathematical model by fitting the mathematical model to the oscillogram while constraining the derivative of the blood volume-transmural pressure relationship in the mathematical model, with respect to transmural pressure, with a maximum near zero and right skewed about the maximum, wherein the signal processor further operates to construct a blood volume waveform for the subject to within a scale factor, determine a blood pressure waveform for the subject by applying the constructed blood volume waveform and the oscillometric waveform to the nonlinear blood volume-transmural pressure relationship; and computes a mean blood pressure for the subject from the determined blood pressure waveform.

10. The apparatus of claim 9 wherein the mathematical model is further defined as $$p_c^{oa}(t) = e\left\{1 + \left[b^{-1}\left([(SP - P_c(t) - a) + b]\left(\frac{c-1}{c+1}\right)^{\frac{1}{c}}\right)\right]^{-c}\right\}^{-1} - e\left\{1 + \left[b^{-1}(DP - P_c(t) - a) + b\left(\frac{c-1}{c+1}\right)^{\frac{1}{c}}\right]^{-c}\right\}^{-1}$$

where t is time; $P_c^{oa}(t)$ is amplitude of oscillations in the measured cuff pressure; $P_c(t)$ is the measure cuff pressure; SP is systolic pressure; DP is diastolic pressure; and a, b, c, and e characterize the nonlinear blood volume-transmural pressure relationship of the subject.

11. The apparatus of claim 9 wherein the blood volume waveform is constructed by:
 subtracting a lower envelope of the cuff pressure oscillations as a function of cuff pressure from the cuff pressure oscillations as a function of cuff pressure to yield a waveform with positive amplitude oscillations; and
 summing the waveform with positive amplitude oscillations with the estimated nonlinear blood volume-transmural pressure relationship evaluated at estimated diastolic pressure.

12. The method of claim 9 wherein the blood pressure waveform is determined by finding the root of the estimated nonlinear blood volume-transmural pressure relationship at different points in time using the constructed blood volume waveform and measured cuff pressure.

13. The apparatus of claim 9 wherein the blood pressure monitor is further defined as a sphygmomanometer.

* * * * *